United States Patent
Martínez et al.

(10) Patent No.: US 8,622,612 B2
(45) Date of Patent: Jan. 7, 2014

(54) METHOD AND APPARATUS FOR DETERMINING THE THERMAL EXPANSION OF A MATERIAL

(75) Inventors: Oscar Eduardo Martínez, Ciudad Autónoma de Buenos Aires (AR); Esteban Alejo Domené, Ciudad Autónoma de Buenos Aires (AR); Nélida Mingolo, Ciudad Autónoma de Buenos Aires (AR); Francisco Balzarotti, Ciudad Autónoma de Buenos Aires (AR); Andrea Verónica Bragas, Ciudad Autónoma de Buenos Aires (AR)

(73) Assignee: Consejo Nacional de Investigaciones Cientificas y Tecnicas (Conicet), Buenos Aires (AR)

(*) Notice: Subject to any disclaimer, the term of this patent is extended or adjusted under 35 U.S.C. 154(b) by 760 days.

(21) Appl. No.: 12/704,879

(22) Filed: Feb. 12, 2010

(65) Prior Publication Data
US 2010/0208242 A1 Aug. 19, 2010

(30) Foreign Application Priority Data
Feb. 12, 2009 (AR) ................................ P090100485

(51) Int. Cl.
*G01N 25/16* (2006.01)
(52) U.S. Cl.
USPC .................. 374/55; 374/57; 374/6; 374/120; 374/130
(58) Field of Classification Search
USPC .................. 374/6, 57, 55, 120, 130
See application file for complete search history.

(56) References Cited

U.S. PATENT DOCUMENTS

| | | | | |
|---|---|---|---|---|
| 4,551,030 A | * | 11/1985 | Luukkala et al. | 374/5 |
| 4,679,946 A | * | 7/1987 | Rosencwaig et al. | 374/5 |
| 4,989,980 A | * | 2/1991 | Berg | 356/496 |
| 5,477,333 A | * | 12/1995 | Shoda et al. | 356/624 |
| 5,479,261 A | * | 12/1995 | Hansen | 356/628 |

(Continued)

*Primary Examiner* — Mirellys Jagan
(74) *Attorney, Agent, or Firm* — Nath, Goldberg & Meyer; Jerald L. Meyer; Scott Langford

(57) ABSTRACT

A focus error signal resulting from the photothermically-induced expansion is measured in a sample of material under analysis. A laser is disposed as a periodically modulated heating source which is directed to the sample and a device for focus error measuring which is directed to the surface being heated. A device measuring focus error generates a signal representative of the displacement of the surface of material in perpendicular direction due to the expansion produced by the periodic heating, which is filtered, either analogically or digitally, to discriminate the displacement component at the frequency in which it was modulated or at any other related frequency, such any harmonic or a sum with any other modulation. The focus error signal, appropriately calibrated, gives a precise and sensitive measure of the magnitude the expansion. Said magnitude and its dependence with the modulation frequency allows the determination of physical properties such as the thermal expansion or thermal diffusivity coefficient, the thickness of a coating film or the absorption coefficient of the light from the heating beam. By varying the wave length of the directed radiation it is possible to determine the absorption spectrum of the sample even for very small sized particles in which the fraction of absorbed energy is very little.

20 Claims, 4 Drawing Sheets

(56) References Cited

U.S. PATENT DOCUMENTS

| | | | |
|---|---|---|---|
| 5,645,351 A * | 7/1997 | Nakata et al. | 374/161 |
| 5,667,300 A * | 9/1997 | Mandelis et al. | 374/43 |
| 5,978,148 A * | 11/1999 | Oono et al. | 359/668 |
| 6,137,640 A * | 10/2000 | Viola | 359/820 |
| 6,756,591 B1 * | 6/2004 | Lounis et al. | 250/316.1 |
| 6,865,034 B1 * | 3/2005 | Willis | 359/820 |
| 6,965,434 B2 * | 11/2005 | Lounis et al. | 356/450 |
| 7,369,334 B2 * | 5/2008 | Case et al. | 359/822 |
| 2002/0011852 A1 * | 1/2002 | Mandelis et al. | 324/752 |
| 2002/0031164 A1 * | 3/2002 | Scheidt et al. | 374/7 |
| 2002/0075776 A1 * | 6/2002 | Kasazumi et al. | 369/47.5 |
| 2002/0094580 A1 * | 7/2002 | Jorgenson et al. | 436/151 |
| 2003/0016338 A1 * | 1/2003 | Yasuda et al. | 355/55 |
| 2004/0188602 A1 * | 9/2004 | Chinn et al. | 250/234 |
| 2005/0190665 A1 * | 9/2005 | Mori et al. | 369/44.17 |
| 2005/0225765 A1 * | 10/2005 | Nicolaides et al. | 356/432 |
| 2006/0114580 A1 * | 6/2006 | Mori et al. | 359/819 |
| 2009/0200279 A1 * | 8/2009 | Li | 219/121.66 |

* cited by examiner

METHOD AND APPARATUS FOR DETERMINING THE THERMAL EXPANSION OF A MATERIAL

TECHNICAL FIELD OF THE INVENTION

The present invention refers to the characterization without contact of materials for use in engineering, particularly steels and other metals, for the measurement of thermal properties at microscopic scales, in particular thermal expansion coefficients, thermal conductivity, thermal diffusivity and film thicknesses, the characterization of optical properties such as absorption spectra and dispersion of very small devices structured in the scale of nanometers to micrometers and the measurement of absorption spectra of very small particles (in the scale of nanometers to millimeter).

PRIOR ART AND PROBLEMS TO BE SOLVED

The determination of thermal parameters (thermal expansion, heat conductivity, thermal diffusivity, etc.) of materials and devices is extremely important to forsee their service applicability. Measurement techniques without contact allow either the detection without damaging the sample or system or the measurement during functioning without disturbing the device. Likewise they allow the remote measurement of parts which are not accessible to contact.

One of the most spread techniques is based on the periodical and transient perturbation of the system by means of electromagnetic heating and the subsequent and simultaneous measurement of caused effects. Photo thermal techniques are known which allow to heat the sample with a pulsed or modulated laser beam and the measurement of the increase in temperature due to emitted infrared radiation by U.S. Pat. No. 5,667,300 and US Patent Applications published under N$^{os}$ 2005/0225765; 2002/0031164 and 2002/0011852. Near variants measure the change in reflectivity of the sample by pulsing a second laser and measuring the reflected intensity, which varies with time due to changes in temperature, allowing for the evaluation of said change in temperature (D. Rocháis et. al., J. Phys. D: Appl. Phys. 38 (2005) 1498-1503; Jon Opsal et. al., J. Appl. Phys. 61(1), Jan. 1, 1987; published US Patent Application N° 2005/0225765). Another variant is to measure the deflection of a beam reflected on the sample which is deviated in respect to the incident beam. The deflection is a measurement of the material deformation, which depends on its expansion coefficient and on the increase of temperature (Jon Opsal et. al., Applied Optics Vol. 22 No. 20, 15 Oct. 1983; Alian Rosencwaig et al, Appl. Phys. Lett. 46(11), Jun. 1, 1985, published US Patent Application N° 2004/0188602). Alternatively the modulated expansion can be measured by means of an optical interferometer (U.S. Pat. Nos. 6,756,591 B1 and 6,965,434 B2). All these techniques require huge equipments which are difficult to align as an argon laser for the heating and an infrared camera for detection, which are connected to computers for the processing and extremely accurate centering of both lasers (heating and measurement) as disclosed in the work by O. E. Martínez et. al., Appl. Phys. B 90, 69-77 (2008).

The relation between the expansion of material due to periodic heating and the properties of test material, such as thermal diffusivity, absorption coefficient, thermal expansion coefficient and heating capacity, is well-known and is described in many works (O. E. Martínez et. al., Appl. Phys. B 90, 69-77 (2008)) thus, once the expansion of material is determined, they can be obtained from this knowledge. In the case of the measurement of opaque film thicknesses there is a previous work (A. Rosenwaig et al. Appl. Phys. Lett. 43, 166 (1983)) in which said thickness is measured from the amplitude of deflection photo thermal signal based on the theory shown for the case of films with different thermal behavior but with the same elastic behavior found in the work of Opsal and Rosenwaig (J. Opsal et al, Thermal wave depth profiling: Theory. J. Appl. Phys. 53, p. 4240, 1982.). Also, it was possible to determine the thickness from the measurement of infrared emission of the sample when heated by an electromagnetic pulse (published US Patent Application N° 2002/0094580).

For the determination of particle absorption spectra and devices, systems based on spectrometers are generally used in which the extinction coefficients are measured (absorption plus dispersion) without distinguishing between both phenomena. For the measurement of light absorption for small particles there is a recent development which allows to measure in the case of particles immersed in a liquid (U.S. Pat. Nos. 6,756,591 B1 and 6,965,434 B2). This is based on the use of photo thermal methods with interferometer in the detection step. Said technique cannot be used in case the particle is in a dry environment, deposited on the surface or in case a nanometric or micrometric device such as the ones used in photonics or microelectronics.

The measurement of the focus error signal, on the other hand, is well developed technology to find and keep the optical reading systems of compact discs (K C Fan et. al., Meas. Sci. Technol. 11 (2000) N1-N7, "Lenk's Laser Handbook" J. D. Lenk, Me Graw-Hill inc. 1992). Said devices show signals as large as one volt per micrometer of displacement and are very strong and tolerant to variations of environment conditions and external movements. The most spread method consists on the use of a four-quadrant detector for recording the beam reflected in the target after passing through a system introducing astigmatism. The beam deformation depends on how far is the surface of the target from the focus of the beam and said deformation unbalance the distribution of power between the four quadrants, quantitatively indicating how far the focus from the target is.

SUMMARY OF THE CLAIMED SUBJECT MATTER

Examples of the present subject matter include a method for determining the thermal expansion of a material through the steps of inducing the heating of the material and measuring the displacement of the surface of the material due to the thermal expansion. The step of measuring the displacement comprises sending a measurement beam on the material and determining the focus error of said measuring beam resulting from said displacement. Said step of inducing the heating comprises irradiating a modulated electrical or magnetic field in time at different frequencies of the wave lengths of visible light. Said electric or magnetic field belongs to the group consisting of X rays, infrared radiation and other part of the electromagnetic spectrum, different from the wave lengths of visible light. The step of inducing the heating comprises irradiating the material with a periodically modulated heating beam.

Furthermore the method includes the step of determining at least one additional physical property of the material from said determination of thermal expansion. Said additional physical property belongs to the group consisting of thermal properties at microscopic scales, including thermal expansion coefficients, thermal conductivity and thermal diffusivity and film thicknesses; optical properties including absorption coefficient of incident light in the heating beam, absorption spectra and dispersion; and coating film thicknesses. Furthermore, the step of determining thermal diffusivity of the material from the measurement of thermal expansion as a function of the modulation frequency in included. The present subject matter has the additional steps of: displacing the beams with relation to a sample and obtaining a spatial map for thermal diffusivity, optical absorption or the thickness of the film on the surface of the sample. Additional steps of varying the wave length of the heating beam and measuring the localized absorption spectrum of the sample are also included.

The determination of an optical property of a material comprising a microscopic or nanoscopic structure, places said microscopic or nanoscopic structures on a transparent substrate of known thermal properties, varying the wave length of the heating beam and measuring the absorption spectrum and dispersion of said microscopic or nanoscopic structure, optical properties such as absorption spectra and dispersion of devices. The additional step of determining the thermal expansion coefficient of the material from the determination of the thermal expansion, the dimensions of the heating beam and the fraction of absorbed energy are also included. The additional step of determining the thickness of the film covering the substrate of the material by measuring the phase of the expansion modulation as a function of the frequency and determining the frequency at which said phase takes maximum or minimum values is part of the present subject matter.

Accordingly, the step of determining the focus error comprises introducing astigmatism in said measurement beam and measuring the elipticity of the beam reflected by the material. The apparatus for determining the thermal expansion of a material using the method of the present subject matter comprises a mechanism of heating with a periodic modulated source and a focus error measuring device capable of determining the displacement of the surface due to the thermal expansion. The mechanism of heating comprises a periodically modulated laser beam source while said focus error measuring device comprises a laser beam source with a different frequency as regards the heating laser beam. Furthermore the mechanism of heating comprises a periodically modulated laser beam source directed to the material while said focus error measuring device comprises a laser beam source also directed to the material and a detector of the beam reflected by said material. In certain embodiments, between the laser beam source of the focus error sensing device and the material there is a means introducing astigmatism in said laser beam and said detector of the reflected beam is capable of measuring the elipticity of the reflected beam. The laser heating beam source and the laser beam source of the device measuring focus error are of different frequencies and are jointly directed towards the same surface of the material. In certain embodiments, the laser heating beam source and the laser beam source of the device measuring focus error are of different frequencies and are jointly directed towards the same surface of material. The source of laser heating beam and the laser beam source of the device measuring focus error are directed on opposite surfaces of the material and said detector of the reflected beam comprises a digital camera. It further includes a detector of error of the beam transmitted by said material.

BRIEF DESCRIPTION OF THE INVENTION

The present invention measures a focus error signal resulting from the expansion photothermically induced in a sample of material under analysis.

A laser is provided or another heating source periodically modulated which is directed to the sample and a device for focus error measuring which is directed on de surface being heated. Due to the expansion produced by the periodic heating, the surface of the material will be displaced in an essentially perpendicular direction thereto, and said displacement is detected by a focus error measuring device. The signal of said device is filtered either electronically or numerically in order to retrieve the component of the displacement to the frequency at which it was modulated or to any other frequency related therewith, as any harmonics or sum with another modulation.

It has been found that said focus error signal, when appropriately calibrated, gives a very accurate and sensitive measurement of the magnitude of the expansion. Said magnitude and its dependence with the modulation frequency allows for the determination either the thermal expansion coefficient, or the thermal diffusivity, the thickness of coating film or the absorption coefficient of light on the heating beam.

By varying the wave length of the incident radiation it is possible to determine the absorption spectrum of sample even for very small particles in which the absorbed energy fraction is very small.

DESCRIPTION OF THE DRAWINGS

In order that the present invention is clearly understood and easily brought into practice it has been shown in one of its preferable embodiments in figures which are only illustrative, and are not limitative to this specification, and in which.

DETAILED ILLUSTRATIVE DESCRIPTION OF THE INVENTION

A mechanism of modulated localized heating in time at a controlled frequency, preferably a laser, produces the periodic expansion of material at the modulation frequency. Said expansion depends on the absorbed power, spatial dimensions of the heating mechanism and the heating frequency, as known, as it was described in prior art. In accordance with the present invention, a focus error sensing device is used for measuring the expansion of the surface, since being it displaced by means of heat, it is set aside of the correct focus as established in the focus error sensing device. The focus error signal is then a measure for displacement of the surface and therefore its thermal expansion.

Figure 1:
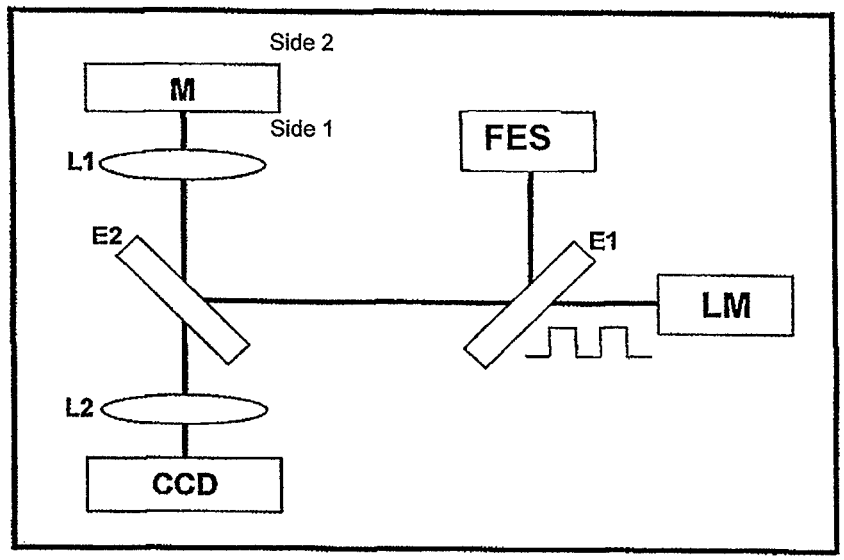
FIG. 1 is a scheme of one possible embodiment for the measurement of thermal properties of opaque surfaces according to the present invention.

FIG. 1 shows an apparatus according to the present invention provided with an LM modulated laser source directed by means of dicroic mirror E1 and a beam splitter E2 to the test sample M. The beam splitter is a mirror E2 which partially reflects the wave length for the emission of LM laser. The laser beam is focused on the sample by a lens L1, preferably a microscope objective. The reflection on the first face (Side 1) of the sample M is directed through the beam splitter E2 to a camera CCD.

The Side 1 of the sample will expand as a consequence of the heating originated by the absorbed energy. The beam of a sensor laser (with a wave length different to the heating LM) which is part of a focus error sensing device FES, is combined with the heating beam by means of a dicroic mirror E1. The detector of the focus error signal FES sends the sensor beam of the position of the surface through the dicroic mirror E1 and mirror E2.

The focus error sensing device typically consists of a laser which is introduced astigmatism such that it does not simultaneously focuses in two perpendicular axes to the same plane perpendicular to the propagation axis and in this way the elipticity of the beam which returns is a measure of how far from the mean focus is the reflecting surface. Typically the elipticity is measured with a four quadrant detector. Said devices are an integral part of optical discs readers and recorders such as CD and DVD. In order to guarantee the quality of the focus and to measure the size of the beam on the surface of the sample, the system is fitted with a camera which records the image of the surface named as Side 1 by means of the lens L2 and likewise it allows for the measurement of the size and shape of the heating beam of LM laser on the surface of the sample. The signal of the focus error sensor FES gives a measure for displacement of the surface due to the thermal expansion.

Figure 2:
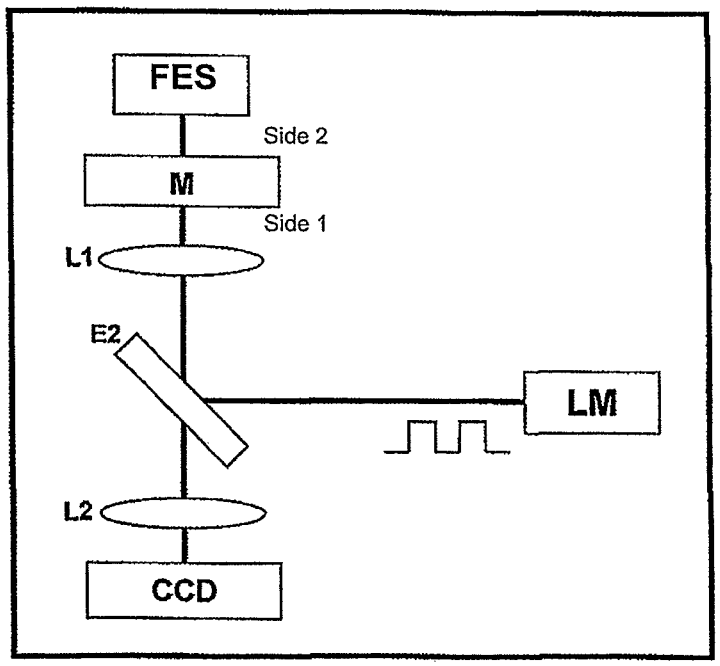
FIG. 2 illustrates a variant of the previous embodiment which is appropriate to measure the thermal properties of a small or thin sample placed on a transparent substrate.

Alternatively, the focus error signal device FES may be placed on the opposite side of the sample M which is reached by the heating beam as shown in FIG. 2, so that the detector device of the focus error signal measures the expansion of Side 2. Sample M is placed on a transparent substrate on the face of Side 2. This alternative embodiment is particularly appropriate if sample is too thin or with very small dimensions.

Figure 3:
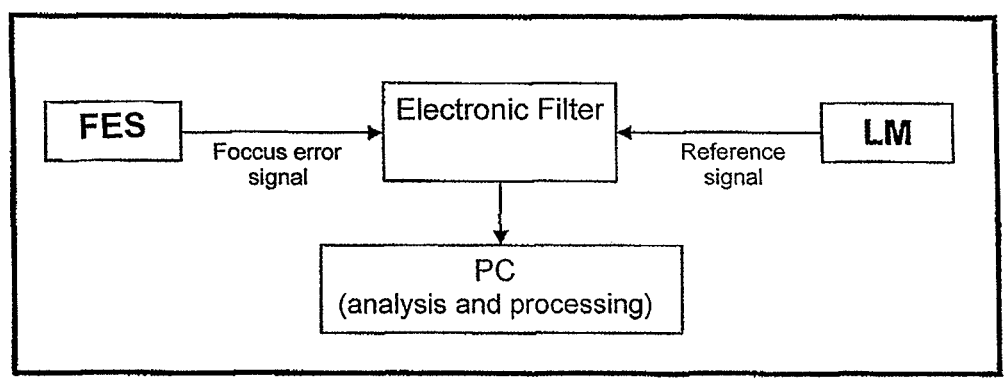
FIG. 3 is a scheme of the connection for the processing of focus error signal.

The focus error signal is electronically filtered, preferably by an amplifier sensitive to the phase as shown in FIG. 3. The electronic filter receives the reference signal of the modulation of LM laser and the focus error signal for processing. Said amplifier receives the reference signal of modulated laser and determines the component of the focus error signal at the modulation frequency in amplitude and phase. Alternatively, this filtering operation may be numerically performed after digitalizing the focus error signal. Another alternative is to place an electronic filter and only measure the amplitude (without the phase) of the focus error signal. The absolute calibration of the displacement may be performed by displacing sample in a controlled way while the focus error signal is recorded. For this, it is necessary to include in the system any controlled displacement mechanism with submicron resolution (not illustrated but it is known by one skilled in the art).

Figure 4:
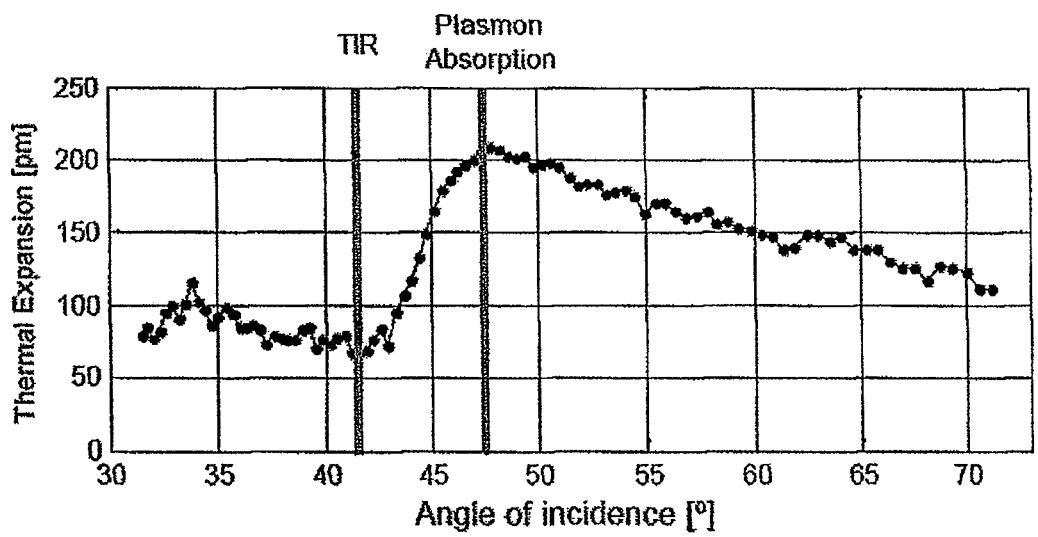
FIG. 4 illustrates the result of a measurement with the embodiment described in FIG. 2 by means of a signal graphics as a function of the incidence angle.

In FIG. 4 it is illustrated the result of a measurement in the embodiment described in FIG. 2 of a gold coating of 10 nm in thickness on a glass substrate of 150 μm in thickness when it is illuminated with a laser of wave length of 532 nm modulated at about 500 Hz. This is a graphic of the signal as a function of the incidence angle to illustrate how the absorption of the sample varies with the angle.

For the determination of thermal expansion, the focus error signal is calibrated for, this way, knowing how the signal varies as a function of the distance. Therefore, the thermal expansion is measured directly recording the changes in the focus error signal.

For the determination of thermal diffusivity either the dependence of the thermal expansion signal with the distance to the heating center may be used, or the dependence in a fixed point with frequency. The expressions which may link the thermal expansion with the diffusivity are well known and may be found in S. M. Landi et. al., J. Ultramicroscopy 77 (1999) and S. M. Landi et. al., J. Appl. Phys., Vol. 88 No. 8, Oct. 15, 2000.

Figure 5:
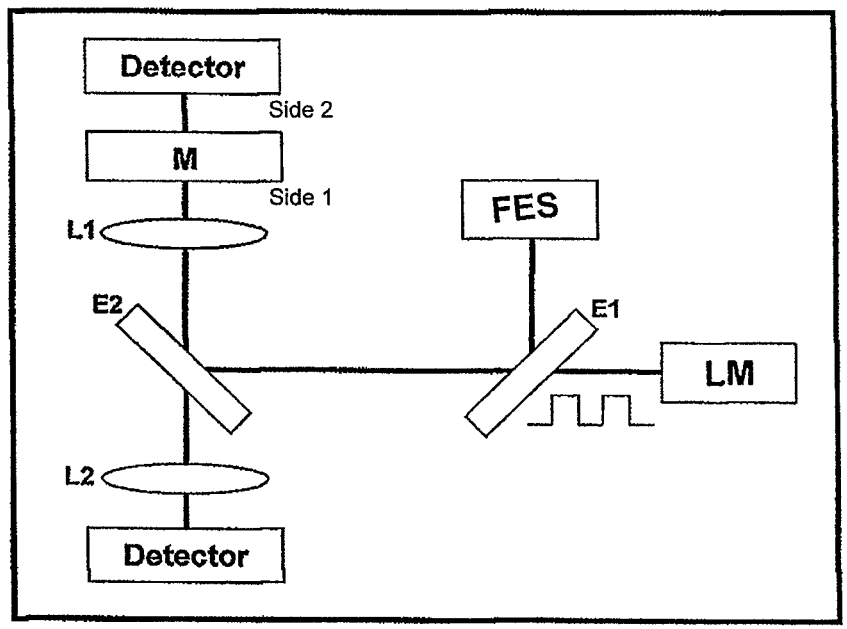
FIG. 5 is a measuring scheme similar to the one for FIG. 1 with the incorporation of both detectors, one for measuring the transmitted power and the other for measuring the reflected power.

Alternatively, the dependence of the absorption coefficient may be measured with the wave length of heating laser (absorption spectrum). For that, it is only necessary to modify the heating laser by placing a luminous source of variable wave length such as a white light laser filtered with a monochromer or a tunable laser. The measurement of the focus error signal as a function of the incident wave length directly provides the absorption spectrum of the sample. If, simultaneously to the absorption, the reflection and the transmission are measured by means of both detectors, as illustrated in FIG. 5, the scattering may be determined by subtraction of the dispersion spectrum of the sample as follows:

$$E_{scattered} = E_{incident} - E_{absorbed} - E_{reflected} - E_{transmitted}$$

where E indicates energy.

Alternatively, for measuring the absorption coefficient for very small particles or microstructures, said particles or structures are placed on a transparent substrate with known thermal properties and the thermal expansion of the substrate is measured due to the heat transferred by said particle or structure which is at its time heated by the modulated heating beam.

According to another embodiment, the heating of the sample may be performed with a laser, an incoherent source of light (LED, lamp, etc.), a non-luminous electromagnetic radiation source (infrared, microwave, X rays, etc.), electric heating by resisting dissipation, by inductive or magnetic losses or any other mechanism producing the periodic heating of the test system.

Additionally to the above, either the sample M may be moved with respect to the measuring beams or the beams as regards the sample and thus a spatial map can be obtained on the surface of the property which is to be measured, either thermal diffusivity, expansion coefficient or absorption coefficient.

Figure 6:
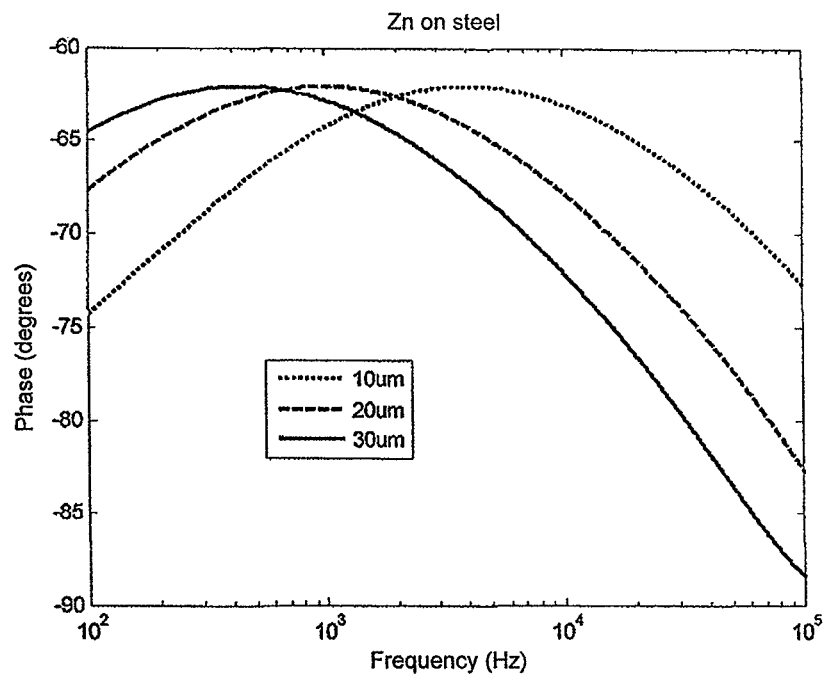
FIG. 6 is a graphic that shows the variation of the modulation phase of the expansion signal as a function of the frequency, for the case of a zinc film (Zn) on a steel sheet.
Figure 7:
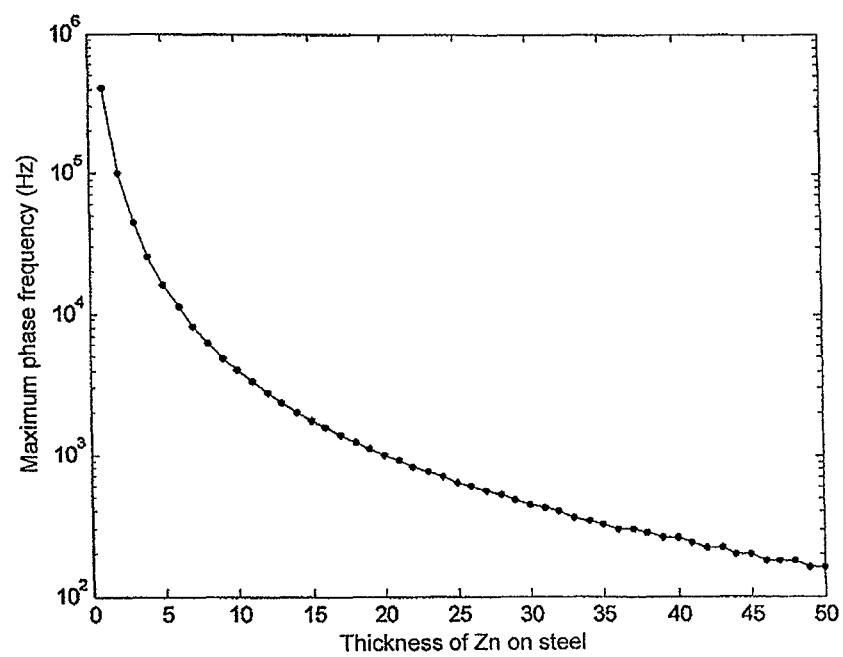
FIG. 7 is a graphic that shows the variation of the frequency at which the maximum of the phase occurs as a function of the thickness of the film for the case of zinc on steel.

For the measurement of thin film thicknesses within the range of nanometers to millimeters it is proposed to use the dependence of the phase for the thermal expansion signal as a function of the modulation frequency in a scheme as illustrated in FIG. 1. In FIG. 6 it is shown how the phase of the thermal expansion signal varies as a function of the frequency, for the case of a zinc film (Zn) on a steel sheet. The presence of a maximum can be observed and the frequency at which this maximum occurs is plotted in FIG. 7 as a function of the thickness of the film. According to the nature of the materials involved (film and substrate) a maximum and a minimum may appear. From graphics as the one of FIG. 7 performed for each pair of materials the value of the thickness of the film may be extracted. This method is much more sensitive to variations in the conditions of the surface than the methods reported before based on the measurement of fixed frequency amplitude.

It is doubtless that when putting the present invention into practice, several modifications can be introduced as needed, but any time they are within the scope and spirit of the invention.

Having described and determined the nature of the invention and the way it can be put into practice, it is claimed, as invention and an exclusive property, as follows:

The invention claimed is:

1. A method for determining thermal expansion of a material comprising the steps of:
    inducing heating of the material; and
    measuring a displacement of a surface of the material due to thermal expansion;
    wherein the step of measuring the displacement comprises sending a measurement beam on the surface of the material and determining a focus error signal of said measuring beam, wherein the focus error signal gives a measure of the displacement of the surface due to thermal expansion.

2. The method of claim 1, wherein the step of determining the focus error further comprises introducing astigmatism in said measurement beam and measuring the elipticity of the beam reflected by the material.

3. The method of claim 1, further comprising the step of determining at least one additional physical property of the material from said determination of thermal expansion.

4. The method of claim 3, further comprising the steps of:
    selecting said additional physical property from the group consisting of thermal expansion coefficients, thermal conductivity, thermal diffusivity, and film thicknesses; and
    determining at least one optical property of the material selected from the group consisting of absorption coefficient of incident light in the heating beam, absorption spectra and dispersion, and coating film thicknesses.

5. The method of claim 4, further comprising the step of determining the thermal expansion coefficient of the material from the determination of the thermal expansion, the dimensions of the heating beam and a fraction of absorbed energy.

6. The method of claim 4, further comprising the step of determining the thickness of a film covering the substrate of the material by measuring a phase of an expansion modulation as a function of frequency and determining the frequency at which said phase takes maximum or minimum values.

7. The method of claim 1, wherein the step of inducing the heating comprises irradiating a modulated electrical or magnetic field in time at different frequencies of wave lengths of visible light.

8. The method of claim 7, further comprising selecting said electric or magnetic field from the group consisting of X rays, infrared radiation and another part of the electromagnetic spectrum different from visible light.

9. The method of claim 7, wherein the step of inducing the heating comprises irradiating the material with a periodically modulated heating beam.

10. The method of claim 9, further comprising the step of determining thermal diffusivity of the material from the measurement of thermal expansion as a function of a modulation frequency.

11. The method of claim 10, further comprising the steps of:
    displacing at least one beam in relation to a sample of the material; and
    obtaining a spatial map for thermal diffusivity, optical absorption or a thickness of a film on a surface of the sample.

12. The method of claim 10, further comprising the steps of:
    varying the wave length of the heating beam; and
    measuring a localized absorption spectrum of the sample.

13. The method of claim 12, further comprising the steps of:
    placing said microscopic or nanoscopic structures on a transparent substrate of known thermal properties;
    varying the wave length of the heating beam; and
    measuring the absorption spectrum and a dispersion of said microscopic or nanoscopic structure.

14. An apparatus for determining the thermal expansion of a material, comprising:
    a mechanism of heating the material with a periodic modulated source; and
    a focus error measuring device configured to determine displacement of a surface of the material due to thermal expansion,
    wherein the mechanism of heating further comprises a periodically modulated first laser beam source; and
    the focus error measuring device further comprises a second laser beam source with a different frequency than a frequency of the first laser beam source.

15. The apparatus of claim 14, wherein:
    the mechanism of heating is configured to direct the first laser beam source to the material;
    the focus error measuring device is configured to direct the second laser beam source to the material; and
    the apparatus further comprises a detector configured to detect at least one beam reflected by the material.

16. The apparatus of claim 15, further comprising:
    means for introducing astigmatism in at least one laser beam, wherein
    the means for introducing astigmatism is between at least one of the first and second laser beam sources and the material; and
    the detector is configured to measure an elipticity of the detected beam.

17. The apparatus of claim 15, wherein the first laser beam source and the second laser beam source are configured to be jointly directed towards a same surface of the material.

18. The apparatus of claim 15, wherein the first laser beam source and the second laser beam source are configured to be directed on opposite surfaces of the material.

19. The apparatus of claim 15, wherein the detector is a digital camera.

20. The apparatus of claim 15, further comprising a detector of error of the at least one beam reflected by said material.

* * * * *